United States Patent [19]

Agerskov et al.

[11] Patent Number: 5,175,428

[45] Date of Patent: Dec. 29, 1992

[54] APPARATUS FOR THE ILLUMINATION OF A REGION OF A BOTTLE OR THE LIKE TO BE INSPECTED SUCH THAT BOTTLE ACTS AS WAVEGUIDE AND SECONDARY LIGHT SOURCE

[75] Inventors: Carsten Agerskov, Killwangen, Switzerland; Henrik Sloth, Vanlose, Ulrik Jacobi, Hellerup, both of Danemark, Sweden; Robert Apter, Dübendorf, Switzerland; Louis-Francois Pau, Ceyreste, France

[73] Assignee: Elpatronic AG, Zug, Switzerland

[21] Appl. No.: 621,228

[22] Filed: Nov. 30, 1990

[30] Foreign Application Priority Data

Dec. 5, 1989 [CH] Switzerland .................. 4351/89

[51] Int. Cl.⁵ ............................................. G01N 9/04
[52] U.S. Cl. ................................. 250/223 B; 356/240
[58] Field of Search ............. 250/223 B; 356/239, 356/240, 428; 209/526, 523; 358/106, 107

[56] References Cited

U.S. PATENT DOCUMENTS

| | | | |
|---|---|---|---|
| 3,394,263 | 7/1968 | Baker | 250/223 B |
| 3,439,178 | 4/1969 | Rottman | 250/223 B |
| 4,025,201 | 5/1977 | Deane | 250/223 B |
| 4,280,624 | 7/1981 | Ford | 250/223 B |
| 4,399,357 | 8/1983 | Dorf et al. | 356/240 |
| 4,437,985 | 2/1984 | Hinds et al. | 356/428 |
| 4,608,709 | 8/1986 | Hedler et al. | 250/223 B |
| 4,664,525 | 5/1987 | Tagaya | 250/223 B |
| 4,679,075 | 7/1987 | Williams et al. | 250/223 B |
| 4,914,289 | 4/1990 | Nguyen et al. | 250/223 B |

Primary Examiner—David C. Nelms
Assistant Examiner—Stephone Allen
Attorney, Agent, or Firm—McCormick, Paulding & Huber

[57] ABSTRACT

The apparatus is used for testing the surface structure of hollow, cylindrical regions of transparent, hollow bodies (e.g. bottles) moved along a track. It comprises an illuminating device (10), a conveyor (14) by means of which the hollow bodies (34) are moved through an inspection region, and an imaging device (12). The illuminating device (10) has several light sources (26) which are arranged so that, in every position within the inspection region (9), the hollow bodies (34) receive light at an angle of incidence such that the hollow bodies (34) act as wave guides and appear as secondary light sources with respect to the imaging device (12), so that the imaging device (12) yields a high-contrast image of the surface structures of the hollow bodies. The device is principally used for the testing of recycled bottles.

23 Claims, 3 Drawing Sheets

APPARATUS FOR THE ILLUMINATION OF A REGION OF A BOTTLE OR THE LIKE TO BE INSPECTED SUCH THAT BOTTLE ACTS AS WAVEGUIDE AND SECONDARY LIGHT SOURCE

BACKGROUND OF THE INVENTION

The invention relates to an apparatus for inspecting a substantially hollow cylindrical region of transparent hollow bodies travelling along a track, whereby the bodies pass through an inspection zone on a section of the track, with an imaging device located on one side of the track including the inspection region, and a light source containing an illumination device located on the opposite side of the track and illuminating the inspection region.

A known device of this type (U.S. Pat. No. 4,691,231) is used for illuminating the sidewalls of bottles which are located on a continuously moving conveyor and are inspected by transmitted light, in order to detect defects in the walls of the bottles. For this purpose, the known device employs six video cameras for the side walls, three more video cameras for a lower side wall region and three video cameras for a side wall region above this. The video cameras may either be arranged in the shape of an arc around the bottle or in a line along the bottle conveyor. The cameras are arranged to provide each time data relating to regions of different height, over the whole circumference of the bottles. To achieve this, diametrically opposed bottle wall regions (front and back sides) are illuminated simultaneously and superimposed on each other. For each pair of cameras arranged one above the other a light source is provided at the side of the bottle opposite the camera; for a total of six cameras there are therefore three light sources. A bottle to be inspected is moved between the first pair of cameras and its corresponding light source and is thus recorded, then between the second pair of cameras and their corresponding light source, and finally between the third pair of cameras and their corresponding light source. A diffusing, transparent plate is disposed between the cameras and the light sources, so that the bottle is more or less equally illuminated for each pair of cameras.

For this known apparatus the illumination comprises illumination purely by transmitted light, for which the rear side and the front side (with respect to the camera) have the same effect on the path of the light beam. Such illumination is not suitable for examining one of the special regions of the bottle, for example the mouth region which is usually provided with a thread, when this is facing the imaging device, since this type of illumination does not give sufficient or uniform contrast to make faults or geometric structures in the glass, e.g. the thread visible. Such a region requires intensive high-contrast and uniform illumination to form the image necessary for inspection, in order that both internal and external defects, such as deposits or changes in the geometry of the glass, can be detected in this region, where the glass surface is very uneven due to the thread. Illumination purely by transmitted light is also unsuitable for inspection if the bottle is filled up to the mouth region with a substantially opaque liquid, or the bottle glass itself is only slightly transparent. The known apparatus therefore only provides for the inspection of bottles made of clear or transparent glass, which also have no thread in the region of the mouth, and which furthermore must not be filled with opaque liquids in this region. Moreover, internal defects in the glass are scarcely illuminated with the known apparatus, because much of the light which travels in the direction of a normal passing through the longitudinal axis of the bottle on to the surface of the bottle is lost by reflection at the surface of the bottle or at water which is present thereon or by refraction. The incident light falls in the normal direction in the known apparatus because the light source and associated camera are always diametrically opposed on opposite sides of the bottle.

SUMMARY OF THE INVENTION

The object of the invention is to develop an apparatus of the type specified at the outset which is capable of providing an image of a region, substantially in the form of a hollow cylinder, of a transparent body with high contrast, in order to make geometric structures or defects in the internal structure of the hollow body more easily visible on inspection.

This object is achieved in apparatus according to the invention in that the light sources are distributed around the inspection region so that the hollow bodies in each position on the track section receive light at such an angle of incidence that the hollow bodies act as waveguides and appear as secondary light sources in relation to the imaging device.

The apparatus according to the invention makes use of the wave-guide effect, and therefore of an effect which was previously mainly used in the field of fiber optics. In this respect that part of the light emitted by the light sources is used which impinges on the wall of the hollow cylindrical region of the hollow body and enters it at such an angle that it is totally reflected when it next impinges on an interface between the material of the hollow body and the air. There is then a high probability of it being totally reflected again, so that the hollow body acts like a wave-guide. On the other hand part of this light which is reflected to and fro inside the hollow body escapes from the latter if it impinges on the interface at an angle less than the critical angle for total reflection. In this way the region of the hollow body to be inspected becomes a secondary light source. Depending on the angle of the surfaces of the hollow body with respect to the cylindrical axis of the hollow cylindrical region, the surfaces of the hollow body which become a secondary light source radiate at different intensities, so that a high-contrast image of the surface of the cylindrical region can be obtained.

This is a highly significant advantage compared with the state of the art, since a particular object of the device according to the invention is not to illuminate a region of the hollow body in which the latter is completely cylindrical in every respect, but to illuminate a region such as the mouth, where the surface of the hollow body exhibits externally projecting structures due to threads, for example, and which according to the invention are displayed and depicted by the imaging device by being illuminated at high contrast so that the hollow body acts as a secondary light source. Likewise cracks, bubbles, etc. in the interior of the material act as interfaces on which light can impinge, so that internal structural defects of this type can also be identified.

In one advantageous embodiment of the invention conveyors, especially circular conveyors, are provided for moving the hollow body through the inspection region. A device may be provided on the conveyors which enables the hollow bodies to be rotated on their path through the inspection region.

The light sources are preferably adjusted amongst themselves with respect to their arrangement and/or their light output so that they illuminate the inspection region homogeneously. The light sources may be adjustable with respect to the distance between them or with respect to their light output. These possibilities of adjustment enable homogeneous illumination of the inspection region to be maintained, for example, in the event of the failure of a light source at any time.

The light sources may be arranged in an arc around the inspection region. Particularly advantageous is apparatus for which light sources of the same light output are arranged equidistant from each other in an arc in the form of a circle around the centre of the inspection region with a radius significantly larger than half the distance between the outermost points of the inspection region, or for which light sources of equal light output are arranged in an arc in the form of a part of an ellipse, the focal points of which are the outermost points of the inspection region, with the distances between the light sources on the elliptical arc inversely proportional to the distance to the nearest focus. The use of light sources of equal output in such arrangements ensures that the inspection region is irradiated with light of approximately homogeneous intensity over the whole of its extent. However it is possible to employ other arrangements of the light sources in order to irradiate the inspection region with light of approximately homogeneous intensity.

Moreover, it is advantageous to arrange a wall of a material which is opaque to light between the light sources and the inspection region, where the wall has an aperture for light to pass through in the shape of an elongated slit extending at perpendicular to the longitudinal axes of the hollow bodies, the vertical dimension of which is at the same height as the height of the regions of the hollow bodies to be inspected and which is larger than the vertical dimension of these regions. These walls may be plane or curved.

Light sources may be used which comprise rod-shaped high-power lamps, parallel to the longitudinal axis of the hollow body, for which the middle light source is opposite to the line which bisects the length of the slit, and their length is at least equal to double the slit height. However light sources may also be used which comprise elongated tubular lamps, each with the shape of a circular or elliptical arc and perpendicular to the longitudinal axis of the bottle.

A row of high-power lamps can be specified for use in the device.

By providing an arc-shaped reflector parallel to an arc-shaped light source arrangement in one embodiment of the invention, additional light energy can be made available in the inspection region. This measure may be further reinforced by a reflecting coating on the wall with the slit on its internal surface which faces the light sources.

Further arc-shaped reflectors ensure that light which would otherwise escape to the outside at the ends of the slit is reflected back into the slit and thereby to the inspection region.

Acting as a secondary light source the hollow, cylindrical region of the hollow body emits light which depicts the surface structure with high contrast. On meeting the imaging device, the light which passes through the hollow cylindrical region of the hollow body without reflection acts as an interfering background for the high-contrast display of the surface structure of the hollow cylindrical part by the secondary light source. This interference is reduced if the imaging device is aligned at the centre of the inspection region, or obliquely with respect to the inspection region, so that it sees the region of the hollow body to be inspected over the whole of the inspection region, but as little as possible of the light sources directly.

BRIEF DESCRIPTION OF THE DRAWINGS

The invention will be described in more detail with the aid of the drawings, in which.

DESCRIPTION OF THE PREFERRED EMBODIMENTS

Figure 1:
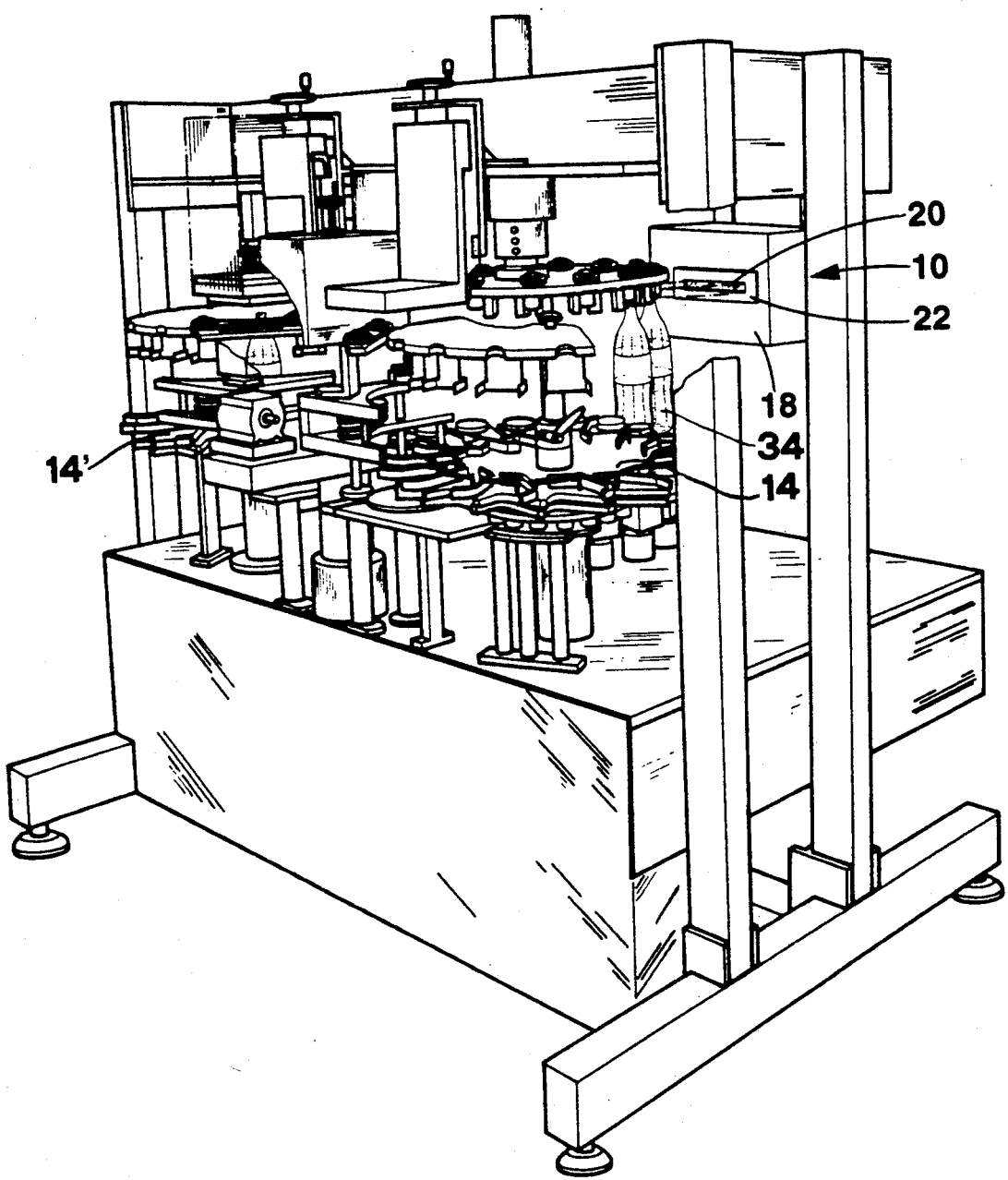
FIG. 1 is an overall view of a bottle testing machine which is provided with the illuminating device according to the invention.

In the drawings the hollow bodies are shown as bottles 34 (FIG. 2), for which the threads in the region of the mouth, and therefore the necks 1 (FIG. 3), are to be examined. The term "bottles" will therefore be used in part below instead of hollow bodies, where the same numeral 34 is used for both. These bottles 34 are examined inside an inspection region 9, which is shown in FIG. 4.

FIG. 1 is an overall view of a bottle examination machine which has an illuminating device 10 for the regions of the mounths of the bottles 34 to be examined.

Instead of being used for the illumination of the mouth regions of bottles which are provided with threads, the device 10 could also be used to illuminate other regions of bottles 34 or other more or less transparent bodies of all types such as hollow glassware, hollow bodies made of PET, etc. The machine has two circular conveyors 14 which deliver the bottles 34 and which move them on two circular tracks, so that various examinations can be made of the bottles 34. Longitudinal conveyors may also be used in such bottle examining machines instead of the circular conveyors 14. The illuminating device 10 is assigned to the circular track 14 on the right of FIG. 1, and has a slit 20 in its front wall 18 which is covered by a glass plate 22. A more detailed drawing of an arrangement according to the invention is shown in FIGS. 2 and 4.

Figure 2:
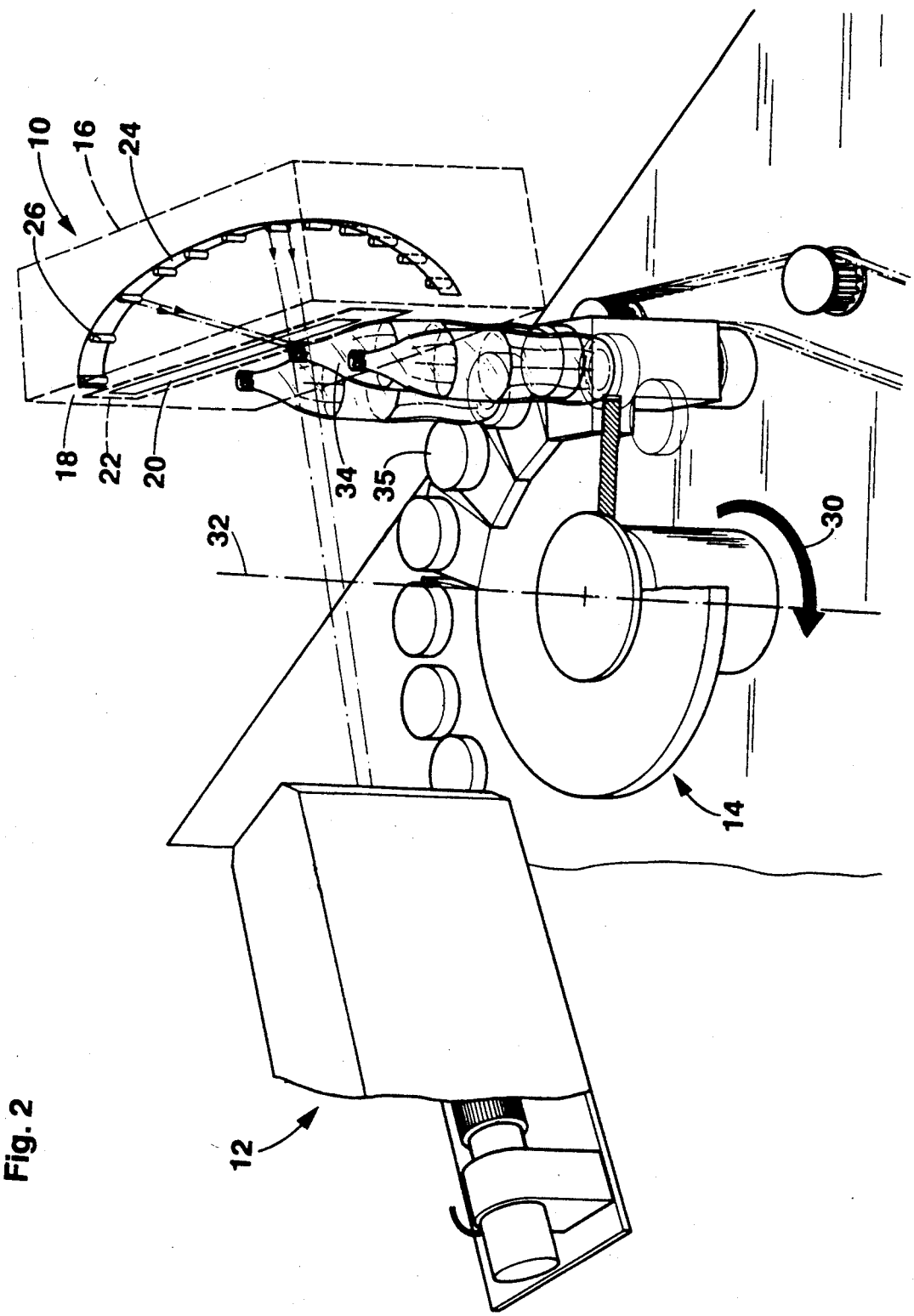
FIG. 2 is a perspective illustration of the device with conveyor and imaging device for inspecting the thread region of bottles.

One of the imaging devices 12 assigned to the illuminating device 10, which is not visible in FIG. 1, is shown in FIG. 2. FIG. 2 also shows in simplified form a circular conveyor 14 which supports the bottles 34.

The illuminating device 10 according to FIG. 2 has a housing 16. This has a front wall 18 made of material which is opaque to light, which is disposed between the light sources 26 provided in the illuminating device 10 and the bottles 34. In the wall 18 there is an elongated slit 20, perpendicular to the longitudinal axis of the bottles 34, the vertical location of which is at the same height as the height of the regions of the hollow bodies 34 to be inspected and the vertical dimension of which is larger than the vertical dimension of these regions. The wall 18 may be plane or curved. The slit 20 is normally open. However under certain conditions it may be covered by a heat-resistant glass plate. A holder 24 is provided in housing 16 for light sources 26. FIG. 2 shows a type of construction for this suitable for rod-shaped high-power lamps, e.g. xenon lamps, parallel to the longitudinal axis of the bottles. The middle one of these light sources 26 is located opposite the line which bisects the slit 20 longitudinally and its length is preferably approximately equal to twice the slit dimension. The light sources 26 are arranged on the holder 24 in the shape of an arc, which is shown as an elliptical arc here. However it could also be a circular arc. The upper and lower ends of the light sources 26 are all arranged at the same height.

The light sources 26 are linked to a power supply, which is not shown, to which they are connected in parallel. The circuit arrangement or the power source is designed so that the light output is adjustable for each light source 26 individually or for all light sources 26 jointly.

The circular conveyor 14 rotates in the direction of the arrow 30 about a central axis 32 and thus moves the bottles 34, which are individually vertically mounted on rotating plates 35 and are rotated clockwise about their longitudinal axes past the illuminating device 10.

In principle, arrangements are also possible in which the light sources 26 are arbitrarily arranged on one side of the track section 15 and of the axes of the hollow bodies 34. However for each arrangement of the light sources 26 it is advantageous to position them so that the light intensity is homogeneous in the inspection region.

Figure 3:
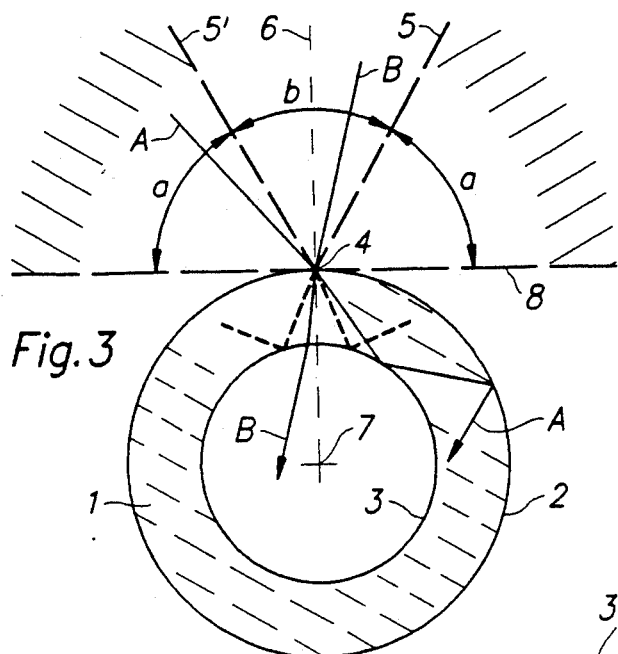
FIG. 3 is an illustration showing the extent of the angle of incidence for which light incident on a point on the surface of the hollow body contributes to the formation of a secondary light source in the hollow body.
Figure 4:
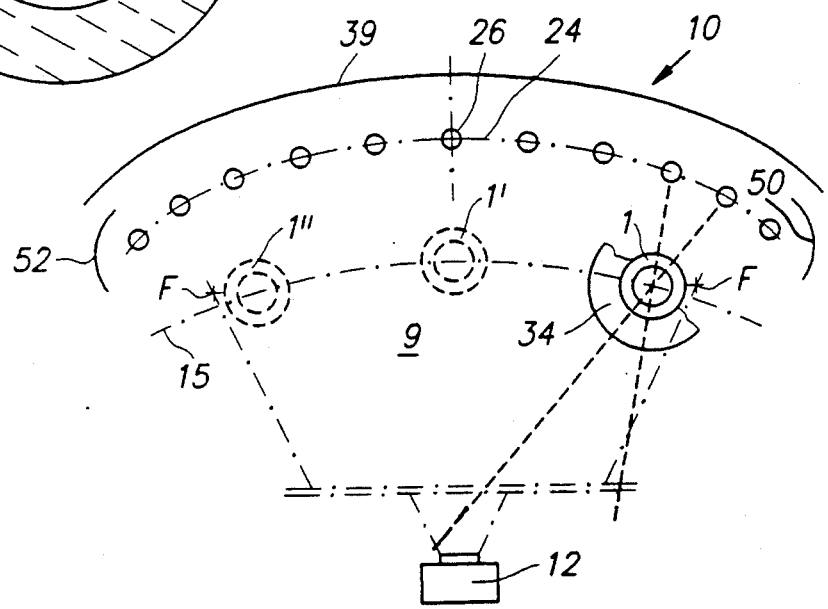
FIG. 4 is a schematic illustration of a preferred embodiment viewed from above.

FIG. 3 shows a bottle neck 1 in cross section; this has an outer surface 2 and an inner surface 3. Light of all angles from a half-space impinges on the bottle neck 1, where the planar limit of the half-space is shown by the line 8. This is considered as the same light which is incident on a point 4 on the outer surface of the bottle neck. Two solid angle regions a, b arise, which are shown in the plane of FIG. 3. Incident light from angular region a contributes to the formation of the secondary light source in the bottle neck; in contrast, incident light from angular region b mainly contributes to the light which passes straight through bottle neck 1. The limiting rays 5,5' separate these angular regions from each other. The limiting rays 5,5' are the same light rays which just attain the critical angle for total reflection at the first interface between the bottle material and the air. For bottle glass with an index of refraction of about $n = 1.5$, the critical angle is about 41°.

A denotes a light ray coming from angular region a which enters the bottle neck 1 at point 4 and impinges on the next interface between the bottle material and the air at an angle greater than the critical angle for total reflection. There is a high probability of it undergoing further total reflections in the bottle neck 1 until it again escapes from this at some point, and thus it contributes to the secondary light source in the bottle neck.

B denotes a light ray coming from angle region b which enters the bottle neck 1 at point 4. It impinges on the interface between the bottle material and the air at an angle less than the critical angle for total reflection, and is transmitted with only a small reflection loss. It thus makes a contribution to the light transmitted through the bottle neck 1.

In the spatial representation, which is not shown here, a right cone of limiting radiation arises, the axis 6 of which goes through point 4 and bottle axis 7. The light sources 26, which are not shown, illuminate the half-space above the bottle neck 1 (shown in FIG. 3), the line 8 thus forms the limit of the illuminated region. If it is considered that the light sources 26, which are preferably arranged in an arc around the inspection region 9 (FIG. 4), preferably illuminate the bottle neck homogeneously, it may be seen that appreciably more light enters the secondary "bottle neck" radiation source and is also emitted by the latter in a high-contrast form than is the case for the transmitted radiation, which interferes with the contrast formation.

To estimate the applicable light intensity over 11 points 4 of the outer surface in the secondary light source and the interfering transmitted intensity, the reflection losses must be taken into account and then integrated over all points 4 to obtain both intensities.

A schematic diagram of a device is shown in FIG. 4 as an example. Track section 15 is provided with an inspection region 9, which is traversed by the bottles 34 (FIG. 2), of which only the cross section of the bottle neck 1 is shown. The bottle neck 1 is located at the right-hand end of inspection region 9, after having passed through the positions corresponding to the bottle necks 1' and 1", which are shown in dashed lines. These positions are now empty. The illuminating device 10 comprises a holder 24, light sources 26 arranged in an elliptical arc, an elliptical reflector 39 which is provided at a location in the illuminating device 10 opposite the inspection region 9, and two further, arc-shaped reflectors 50 and 52 provided at both ends of the elliptical arc. These reflectors increase the optical efficiency of the illuminating device 10. The focal points F of the ellipse formed by the light sources 26 are the limits of the inspection region 9. The reflectors may also be provided on the outer or inner walls of the light sources 26.

The imaging device 12 is provided on the opposite side of the illuminating device 10 with respect to the inspection region 9. In this example it is located at the centre of the inspection region 9 and adjusted so that it just takes in the whole inspection region 9. At the instant corresponding to the drawing, the imaging device 12 only sees the bottle neck 1 located at the position on the right, since the positions of the bottle necks 1' and 1" are already empty. Because of its alignment the imaging device 12 only receives very little transmitted light, but only sees the bottle neck 1 essentially as a secondary source which is illuminating the structure of its surface with high contrast.

The same considerations also apply to the positions 1' and 1" and for all the intermediate positions in inspection region 9. It is therefore evident that, at every position in the inspection region 9, light is received at an angle of incidence such that the hollow body 34 acts as a secondary light source with respect to the imaging device 12.

High-power lamps, such as xenon lamps, halogen lamps or sodium vapour lamps, may be used as light sources 26. In addition, high-pressure or low-pressure lamps may be used. It is important that the lamps provide a high light intensity.

Moreover, the arc on which the light sources 26 are arranged may also comprise a semicircle around the mid-point of the inspection region 9, with a radius significantly larger than half the distance between the outermost points of the inspection region.

Figure 5:
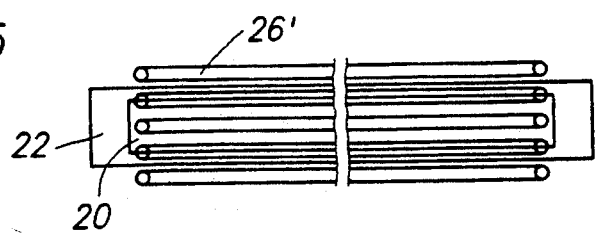
FIG. 5 is a partial front view of a further embodiment of the device.
Figure 6:
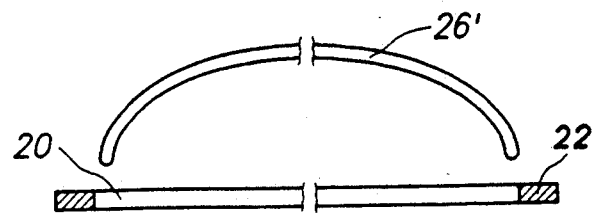
FIG. 6 is the form of construction according to FIG. 5 in plan view.

FIGS. 5 and 6 comprise schematic representations in front view and in plan view of an advantageous type of design of elongated light sources 26', which are each shaped as a semi-ellipse and comprise tubular lamps arranged perpendicular to the longitudinal axis of the bottles. The light sources 26' are also arranged with respect to each other at such distances apart that they provide a homogeneous light intensity in the inspection region 9 (FIG. 4).

In order that a single imaging device 12 may cover the total perimeter of the bottle neck 1, the bottle 34 is advantageously rotated during its progress through the inspection region 9.

The device according to the invention produces a secondary light source in the substantially hollow and cylindrical regions of hollow bodies 34 which are to be inspected, for example in bottle necks 1, and suppresses the interfering transmitted radiation. This makes it possible to display the surface structures and the like of the regions to be inspected, at high contrast, by means of the imaging device 12.

We claim:

1. Apparatus for inspecting a substantially hollow, cylindrical region of transparent hollow bodies moved along a track, wherein the hollow bodies pass through an insepection region on a track section where an imaging device covering the insepection region is located on one side of the track section and the axes of the hollow bodies, and an illuminating device containing light sources which irradiate the inspection region is arranged on the opposite side of the track section, characterized in that the light sources are distributed around the insepection region so that the hollow bodies receive light at each position in the inspection region at an angle of incidence greater than the critical angle for total reflection such that the hollow bodies act as waveguides and appear as secondary light sources with respect to the imaging device.

2. Apparatus according to claim 1, characterized in that a conveyor is provided for moving the hollow bodies along the track.

3. Apparatus according to claim 2, characterized in that the conveyor is a circular conveyor.

4. Apparatus according to claim 2, characterized in that a device is provided at the conveyor which allows the hollow bodies to rotate on their path through the inspection region.

5. Apparatus according to claim 1, characterized in that the light sources are balanced with respect to their arrangement and/or light output so that they illuminate the inspection region homogeneously.

6. Apparatus according to claim 5, characterized in that the distance between the light sources is adjustable.

7. Apparatus according to claim 5, characterized in that the light output of each light source is adjustable.

8. Apparatus according to claim 1, characterized in that the light sources are arranged in an arc around the inspection region.

9. Apparatus according to claim 8, characterized in that the light source with the same light output are arranged equidistantly in an arc in the form of a circle around the centre of the inspection region where the radius of the circle is appreciably larger than half the distance between the outermost points of the inspection region.

10. Apparatus according to claim 8, characterized in that light sources with the same light output are arranged in an arc in the form of a part of an ellipse, in which the focal points (F) of the ellipse are the outermost points of the inspection region and the distances between the light sources on the elliptical arc are inversely proportional to the distance to the respective nearest focal point (F) of the ellipse.

11. Apparatus according to claim 1, characterized in that a wall or material opaque to light is arranged between the light sources and the inspection region, which has an aperture for light to pass through in the form of an elongated slit extending perpendicular to the longitudinal axes of the hollow bodies, the vertical location of which is at the same height as the height of the regions of the hollow bodies to be inspected and the vertical dimension of which is larger than the vertical dimension of these regions.

12. Apparatus according to claim 11, characterized in that the wall is planar.

13. Apparatus according to claim 11, characterized in that the wall is curved.

14. Apparatus according to claim 1, characterized in that the light sources are rod-shaped lamps arranged parallel to the axis of the hollow cylindrical regions of the hollow bodies (34).

15. Apparatus according to claim 11 characterized in that the light sources are parallel high-power lamps, the middle one of which is situated opposite to the line which longitudinally bisects the slit and the length of which is at least equal to twice the vertical dimension of the slit.

16. Apparatus according to claim 9 characterized in that the light sources are elongated tubular lamps, each having the form of a circular or elliptical arc, and extending perpendicular to the axes of the hollow bodies.

17. Apparatus according to claim 1, characterized in that the light sources are xenon lamps.

18. Apparatus according to claim 1, characterized in that the light sources are halogen lamps.

19. Apparatus according to claim 1, characterized in that the light sources are fluorescent tubes.

20. Apparatus according to claim 8, characterized in that an arc reflector is provided on the side of the arc of the light sources remote from the hollow bodies (34).

21. Apparatus according to claim 20, characterized in that a further, arc-shaped reflector is arranged at each end of the arc comprising the light sources.

22. Apparatus according to claim 1, characterized in that the imaging device is disposed vertically at the centre of the inspection region.

23. Apparatus according to claim 1, characterized in that the imaging device is disposed obliquely at the centre of the inspection region.

* * * * *

UNITED STATES PATENT AND TRADEMARK OFFICE
CERTIFICATE OF CORRECTION

PATENT NO. : 5,175,428
DATED : December 29, 1992
INVENTOR(S) : Agerskov, et al

It is certified that error appears in the above-indentified patent and that said Letters Patent is hereby corrected as shown below:

On the title page, the following two inventors names & address should appear as follows: Item [75]: Inventors:  Henrik Sloth
Vanlose, Denmark Ulrik Jacobi
Hellerup, Denmark Signed and Sealed this Fourteenth Day of December, 1993

Attest:

BRUCE LEHMAN

*Attesting Officer*      *Commissioner of Patents and Trademarks*